(12) United States Patent
Hamada et al.

(10) Patent No.: US 9,913,569 B2
(45) Date of Patent: Mar. 13, 2018

(54) DISPLAY CONTROL DEVICE AND ENDOSCOPE SYSTEM

(71) Applicant: OLYMPUS CORPORATION, Hachioji-shi, Tokyo (JP)

(72) Inventors: Toshihiro Hamada, Fuchu (JP); Tatsuhiko Suzuki, Hino (JP); Tomoki Iwasaki, Fuchu (JP); Susumu Hashimoto, Hachioji (JP); Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/347,424

(22) Filed: Nov. 9, 2016

(65) Prior Publication Data

US 2017/0055808 A1    Mar. 2, 2017

Related U.S. Application Data

(63) Continuation of application No. PCT/JP2015/084891, filed on Dec. 14, 2015.

(30) Foreign Application Priority Data

Dec. 15, 2014    (JP) ................ 2014-253092

(51) Int. Cl.
*H04N 9/64* (2006.01)
*H04N 7/18* (2006.01)
(Continued)

(52) U.S. Cl.
CPC .............. *A61B 1/0005* (2013.01); *A61B 1/04* (2013.01); *G02B 23/24* (2013.01);
(Continued)

(58) Field of Classification Search
None
See application file for complete search history.

(56) References Cited

U.S. PATENT DOCUMENTS 7,995,045 B2 * 8/2011 Dunki-Jacobs .......... G09G 5/00
   345/204
8,558,879 B2 * 10/2013 Doi ........................ H04N 7/183
   348/65
(Continued)

FOREIGN PATENT DOCUMENTS

JP    H02-286124 A    11/1990
JP    H07-306930 A    11/1995
(Continued)

OTHER PUBLICATIONS

Feb. 23, 2016 International Search Report issued in International Patent Application No. PCT/JP2015/084891.
(Continued)

*Primary Examiner* — Reza Aghevli
(74) *Attorney, Agent, or Firm* — Oliff PLC

(57) ABSTRACT

A display control device comprises an image acquiring unit which acquires observation image data, an image recording unit which records recorded image data, an image synthesizing unit which generates synthesized image data based on the observation image data and the recorded image data, a first selector, a second selector, and a selector interlock controller. The first selector outputs one of the observation image data and the synthesized image data to a first display device as first selected data. The second selector outputs one of the first selected data and the recorded image data to a second display device as second selected data. The selector interlock controller interlocks and controls the first selector 122 and the second selector 124.

11 Claims, 7 Drawing Sheets

(51) Int. Cl.
*H04N 7/01* (2006.01)
*H04N 5/235* (2006.01)
*A61B 1/00* (2006.01)
*A61B 1/04* (2006.01)
*G02B 23/24* (2006.01)
*H04N 5/232* (2006.01)
*H04N 5/272* (2006.01)
*H04N 5/225* (2006.01)

(52) U.S. Cl.
CPC ..... *G02B 23/2484* (2013.01); *H04N 5/23254* (2013.01); *H04N 5/23293* (2013.01); *H04N 5/272* (2013.01); *H04N 7/183* (2013.01); *H04N 9/646* (2013.01); *H04N 7/0117* (2013.01); *H04N 2005/2255* (2013.01)

(56) References Cited

U.S. PATENT DOCUMENTS 8,858,429 B2* 10/2014 Mizuyoshi ........... A61B 1/0653
600/118

2005/0078175 A1* 4/2005 Kaneko ............ A61B 1/00009
348/65
2009/0193299 A1* 7/2009 Sekiguchi .......... A61B 1/00039
714/48
2015/0054929 A1* 2/2015 Ito .......................... A61B 1/273
348/65

FOREIGN PATENT DOCUMENTS

| JP | H09-131308 A | 5/1997 |
| JP | H10-276973 A | 10/1998 |
| JP | 2000-245692 A | 9/2000 |
| JP | 2005-111081 A | 4/2005 |
| JP | 2007-252688 A | 10/2007 |
| JP | 2012-105738 A | 6/2012 |
| JP | 2013-162874 A | 8/2013 |

OTHER PUBLICATIONS

Jun. 29, 2017 Notification of Transmittal and Translation of IPRP issued in International Application No. PCT/JP2015/084891.

* cited by examiner

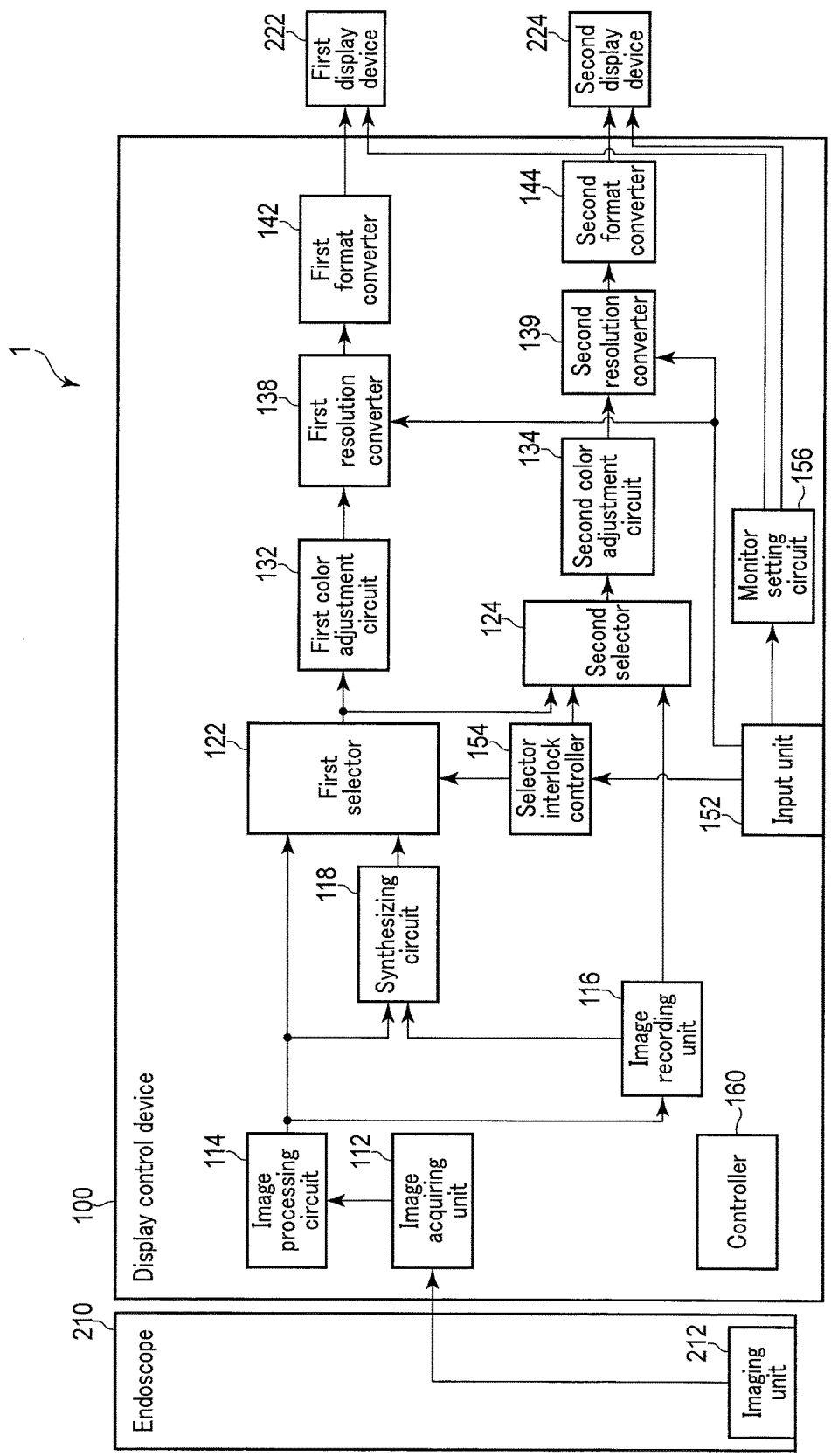
F I G. 3

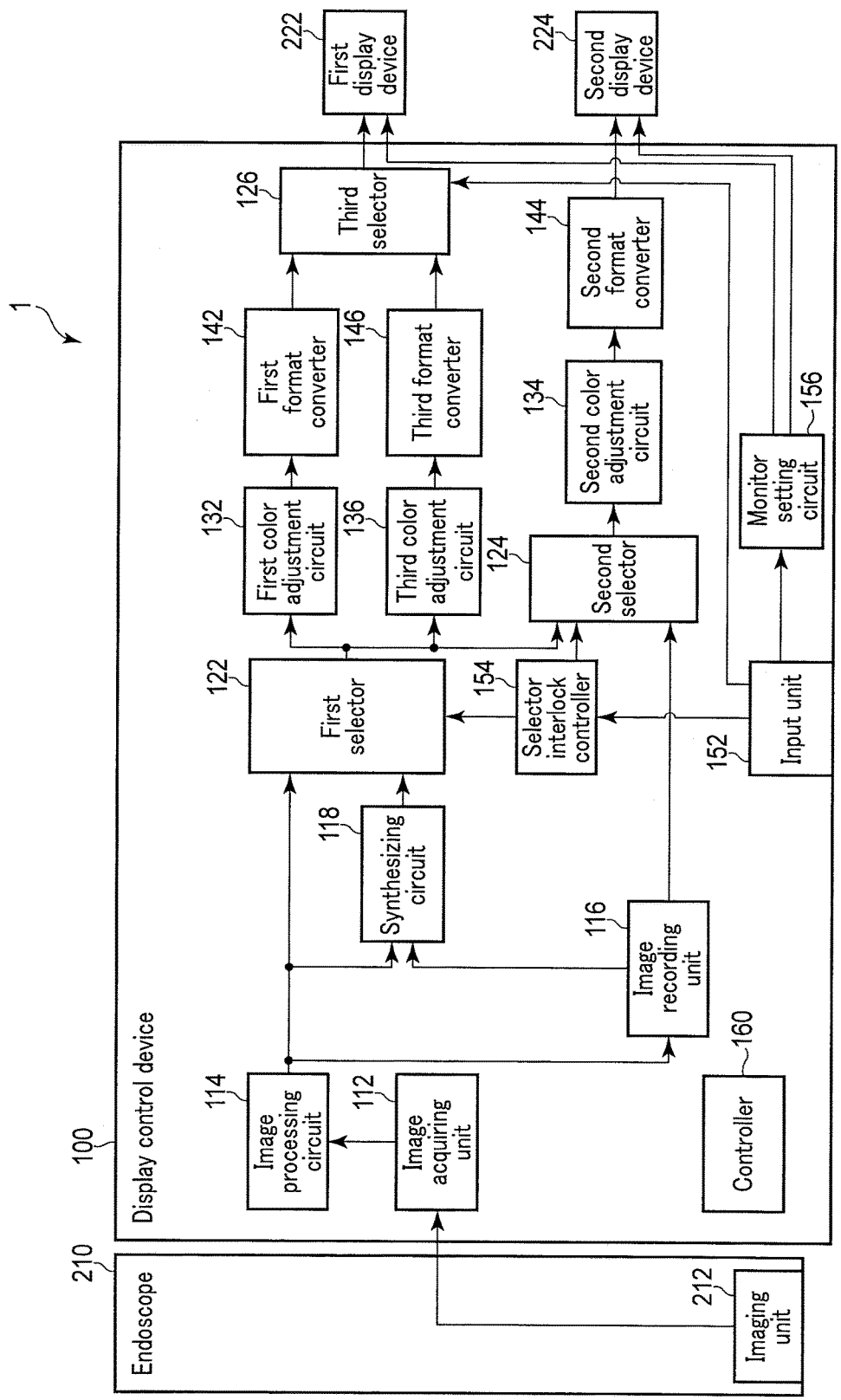
F I G. 5

DISPLAY CONTROL DEVICE AND ENDOSCOPE SYSTEM

CROSS-REFERENCE TO RELATED APPLICATIONS

This application is a Continuation application of PCT Application No. PCT/JP2015/084891, filed Dec. 14, 2015 and based upon and claiming the benefit of priority from prior Japanese Patent Application No. 2014-253092, filed Dec. 15, 2014, the entire contents of all of which are incorporated herein by reference.

BACKGROUND OF THE INVENTION

1. Field of the Invention

The present invention relates to a display control device for an endoscope and an endoscope system.

2. Description of the Related Art

An electronic endoscope which displays an image imaged by an image sensor on a display device has been widely used in the medical field. An endoscope system which comprises a display device for displaying various images in addition to a display device that displays observation images of the endoscope is known. For example, Jpn. Pat. Appln. KOKAI Publication No. 2005-111081 discloses a technique related to an endoscope system which displays a virtual image together with a live image.

BRIEF SUMMARY OF THE INVENTION

According to an embodiment of the present invention, a display control device for an endoscope comprises an image acquiring unit which acquires observation image data from an imaging unit provided on the endoscope; an image recording unit which records recorded image data; an image synthesizing unit which generates synthesized image data representing a synthesized image obtained by synthesizing an image based on the observation image data and an image based on the recorded image data, based on the observation image data and the recorded image data; a first selector which selects one of the observation image data and the synthesized image data as first selected data, and outputs the first selected data to be displayed on a first display device; a second selector which selects one of the first selected data and the recorded image data recorded in the image recording unit as second selected data, and outputs the second selected data to be displayed on a second display device; and a selector interlock controller which interlocks and controls the first selector and the second selector.

According to an embodiment of the present invention, an endoscope system comprises the above-mentioned display control device; the endoscope; the first display device; and the second display device.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a block diagram showing a schematic exemplary configuration of an endoscope system according to a second embodiment;

FIG. 5 is a block diagram showing a schematic exemplary configuration of an endoscope system according to a third embodiment.

DETAILED DESCRIPTION OF THE INVENTION

First Embodiment

Figure 1:
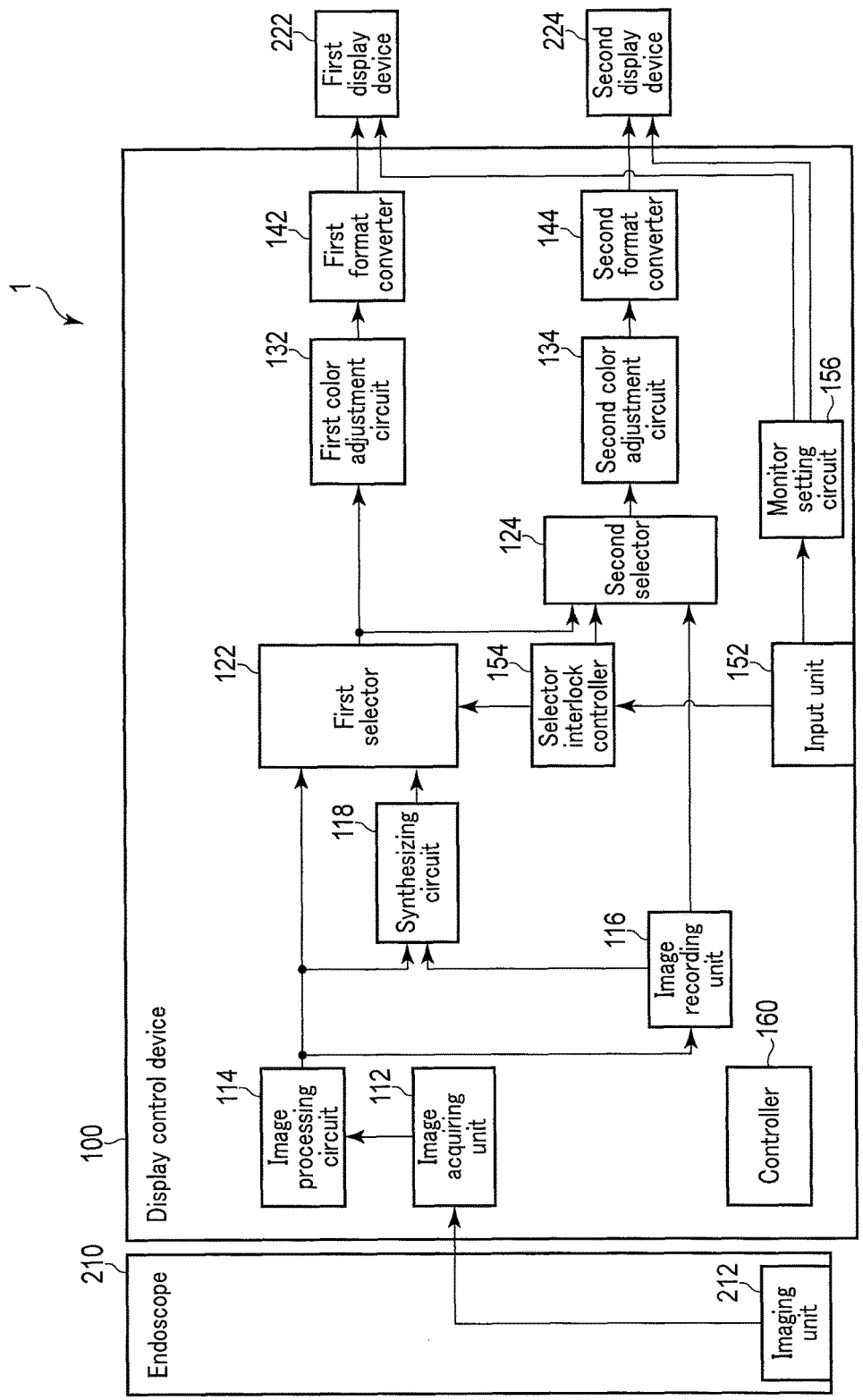
FIG. 1 is a block diagram showing a schematic exemplary configuration of an endoscope system according to a first embodiment.

A first embodiment of the present invention will be explained with reference to the drawings. A schematic exemplary configuration of an endoscope system 1 according to the present embodiment is shown in FIG. 1. The endoscope system 1 comprises an endoscope 210, a display control device 100, a first display device 222, and a second display device 224.

The endoscope 210 comprises an elongated insertion part, and has an imaging unit 212 provided on the distal end portion of the insertion part. The imaging unit 212 performs imaging operations and generates a video signal. The imaging unit 212 outputs the generated video signal to the display control device 100.

The first display device 222 and the second display device 224 are general display devices such as a liquid crystal display. The first display device 222 functions as a main monitor, and the second display device 224 functions as a sub-monitor. In the above manner, the endoscope system 1 comprises two display devices.

The display control device 100 performs control related to displaying on the first display device 222 and the second display device 224 the image acquired by the endoscope 210. The display control device 100 comprises an image acquiring unit 112, an image processing circuit 114, an image recording unit 116, a synthesizing circuit 118, a first selector 122, a second selector 124, a first color adjustment circuit 132, a second color adjustment circuit 134, a first format converter 142, a second format converter 144, an input unit 152, a selector interlock controller 154, a monitor setting circuit 156, and a controller 160.

The image acquiring unit 112 acquires a video signal from the imaging unit 212 of the endoscope 210. The image acquiring unit 112 outputs the acquired video signal to the image processing circuit 114. The image processing circuit 114 applies general image processing on the video signal acquired from the image acquiring unit 112. The image processing circuit 114 outputs the image data that was image processed to the image recording unit 116, the synthesizing circuit 118, and the first selector 122 as appropriate. The image represented by the image data output from the image processing circuit 114 is the image acquired at this point at the imaging unit 212 of the endoscope 210, which would be referred to as an observation image.

The image recording unit 116 includes a general storage medium. The image recording unit 116 records the image data acquired from the image processing circuit 114 that was image processed. Here, the image data to be recorded is still image data representing, for example, a still image. The image data recorded in the image recording unit 116 is output to the synthesizing circuit 118 or the second selector 124 as requested. The image represented by the image data output from the image recording unit 116 will be referred to as a recorded image.

The image recorded in the image recording unit 116 may also be an image acquired by other endoscope systems. The image recorded in the image recording unit 116 may also be an image temporarily read out from a memory when a freeze operation is performed at the endoscope 210. The image recorded in the image recording unit 116 is not limited to an image acquired using an endoscope, and may also be an image acquired by other equipment, or computer graphics, etc.

The synthesizing circuit 118 functions as an image synthesizing unit which creates a synthesized image. The synthesizing circuit 118 creates a synthesized image by synthesizing an observation image acquired from the image processing circuit 114, which was imaged by the imaging unit 212 at that point, and a recorded image acquired from the image recording unit 116, which was, for example, imaged by the imaging unit 212 in the past. The synthesized image is, for example, an image obtained by arranging side by side an image acquired from the image processing circuit 114 and an image acquired from the image recording unit 116. By such image in which the observation image and the recorded image are arranged side by side, a user would be able to easily compare both images. The synthesizing circuit 118 outputs the image data of the created synthesized image to the first selector 122.

Under the control of the selector interlock controller 154, the first selector 122 selects one of the image data of the observation image acquired from the image processing circuit 114 and the image data of the synthesized image acquired from the synthesizing circuit 118. The first selector 122 outputs the selected data as first selected data to the second selector 124 and the first color adjustment circuit 132.

Under the control of the selector interlock controller 154, the second selector 124 selects one of the first selected data acquired from the first selector 122 and the image data of the recorded image acquired from the image recording unit 116. The second selector 124 outputs the selected data as second selected data to the second color adjustment circuit 134.

The first color adjustment circuit 132 performs color adjustment processing on the image data to adjust the color of the image represented by the input image data. This color adjustment processing is a color adjustment performed in accordance with the characteristics of the first display device 222. The first color adjustment circuit 132 outputs the color adjusted image data to the first format converter 142.

The first format converter 142 performs processing for converting the transmission standard of the video signal. In other words, in compliance with the signal transmission standard to which the first display device 222 corresponds, the first format converter 142 performs processing on the image data acquired from the first color adjustment circuit 132 to comply with the transmission standard of the first display device 222. Here, the signal transmission standard may be, for example, a Serial Digital Interface (SDI) or a Digital Visual Interface (DVI). For example, a plurality of types of terminals corresponding to the transmission standards are prepared in the first format converter 142. The first display device 222 is connected to a terminal corresponding to the transmission standard used by the first display device 222 among a plurality of terminals. The first format converter 142 converts the transmission standard in compliance with the terminal to which the first display device 222 is connected. The first format converter 142 outputs the converted image data to the first display device 222, and has the image represented by the image data displayed on the first display device 222.

In the same manner as the first color adjustment circuit 132, the second color adjustment circuit 134 performs color adjustment processing on the input image data. This color adjustment processing is a color adjustment performed in compliance with the characteristics of the second display device 224. The second color adjustment circuit 134 outputs the color adjusted image data to the second format converter 144.

In the same manner as the first format converter 142, the second format converter 144 performs conversion of the transmission standard of the video signal. In other words, in compliance with the signal transmission standard to which the second display device 224 corresponds, the second format converter 144 performs processing on the image data acquired from the second color adjustment circuit 134 to comply with the transmission standard of the second display device 224. The second format converter 144 outputs the converted image data to the second display device 224, and has the image represented by the image data displayed on the second display device 224. The transmission standard of the first display device 222 and the transmission standard of the second display device 224 may be different or the same.

By conducting color adjustments by the first color adjustment circuit 132 and the second color adjustment circuit 134, images of the same color tone would be displayed on the first display device 222 and the second display device 224 which have different characteristics.

The input unit 152 is a section for acquiring instructions from a user. The input unit 152 is, for example, a button, a dial, a keyboard, or a touch panel. The input unit 152 outputs the acquired user's instruction to the selector interlock controller 154, the monitor setting circuit 156, and the controller 160, etc.

Based on the user's instruction acquired from the input unit 152, the selector interlock controller 154 interlocks the selecting operation of the image data performed by the first selector and the selecting operation of the image data performed by the second selector 124, and controls them.

The monitor setting circuit 156 sets the setting values of the first display device 222 and the second display device 224. The monitor setting circuit 156 sets the first display device 222 and the second display device 224 so that images in the same color tone, etc. are displayed on the first display device 222 and the second display device 224 which have different characteristics.

The controller 160 is connected to each unit of the display control device 100, and controls the operation of each unit of the display control device 100. The controller 160 comprises a Central Processing Unit (CPU) or an Application Specific Integrated Circuit (ASIC), etc. and performs various calculations. The operation of the controller 160 is performed in accordance with a program recorded in an unillustrated recording unit. In FIG. 1, the illustration of a line indicating the connection between the controller 160 and each unit in the display control device 100 is omitted.

An operation of the endoscope system 1 according to the present embodiment will be explained in the following. The present embodiment comprises a first mode and a second mode for image display. In the first mode, the observation image is displayed on the first display device 222, and the recorded image is displayed on the second display device 224. In the second mode, the synthesized image is displayed on the first display device 222, and the synthesized image is also displayed on the second display device 224.

Figure 2:
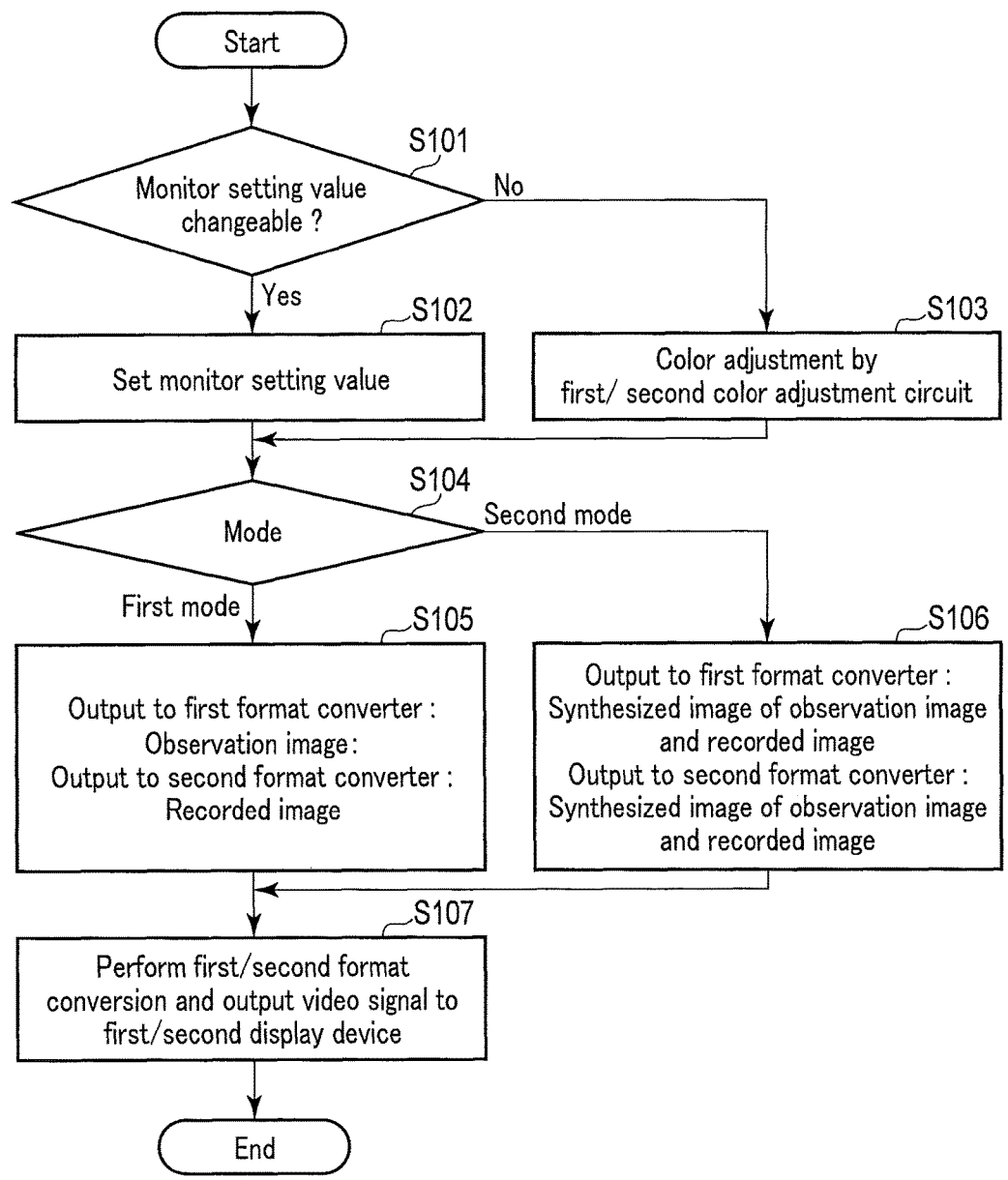
FIG. 2 is a flowchart showing an example of a display control by a display control device according to the first embodiment.

The operation relating to the setting of the image display of the endoscope system 1 according to the present embodiment will be explained with reference to the flowchart shown in FIG. 2.

In step S101, the controller 160 determines whether or not a monitor setting value of the first display device 222 or the second display device 224 can be changed by the monitor setting circuit 156. For example, if the first display device 222 or the second display device 224 is a display device dedicated to the endoscope system 1, the setting value may be changed for such display device by the display control device 100. When it is determined that the monitor setting value can be changed, the processing proceeds to step S102.

In step S102, the controller 160 has the monitor setting circuit 156 set the monitor value of the first display device 222 and/or the second display device 224. Here, the monitor setting circuit 156 sets the brightness, contrast, color tone, etc. of the display device so that the image displayed by the first display device 222 and the image displayed by the second display device 224 are displayed in a similar manner. Generally, even if the same image data is input, depending on the setting of the display devices, the image actually displayed on the display devices may differ. In the present embodiment, for example, the monitor setting circuit 156 sets the monitor setting value so that the same image is displayed on the first display device 222 and the second display device 224 if the same image data is input to the first display device 222 and the second display device 224. Subsequently, the processing proceeds to step S104.

When it is determined that the monitor setting value cannot be changed in the determination of step S101, the processing proceeds to step S103. In step S103, the controller 160 sets the first color adjustment circuit 132 and/or the second color adjustment circuit 134 so as to perform color adjustment. In other words, the controller 160 acquires information regarding the characteristics of the first display device 222 and the second display device 224. The controller 160 sets the setting value for the color adjustment to be performed by the first color adjustment circuit 132 and/or the second color adjustment circuit 134 in a manner that the same image is displayed on the first display device 222 and the second display device 224 if the same image data is input to the first display device 222 and the second display device 224. In other words, the set setting value is a setting value for performing color adjustment in a manner that would cancel the difference in characteristics between the first display device 222 and the second display device 224. Subsequently, the processing proceeds to step S104.

Even in the case where the monitor setting value can be changed, the color adjustment may be performed by the first color adjustment circuit 132 and the second color adjustment circuit 134 together with the changing of the setting value of the first display device 222 and/or the second display device 224 by the monitor setting circuit 156.

In step S104, the controller 160 acquires the user's input to the input unit 152 and determines the selected display mode. When it is determined that the first mode is selected, the processing proceeds to step S105.

In step S105, the controller 160 instructs the selector interlock controller 154 to have the first selector 122 select the observation image between the observation image and the synthesized image as the first selected data. The first selector 122 acquires the image data of the observation image from the image processing circuit 114, and outputs this observation image data to the first color adjustment circuit 132 and the second selector 124. As a result, the observation image is displayed on the first display device 222 via the first color adjustment circuit 132 and the first format converter 142.

Furthermore, in step S105, the controller 160 instructs the selector interlock controller 154 to have the second selector 124 select the recorded image between the observation image and the recorded image as the second selected data. The second selector 124 acquires the image data of the recorded image from the image recording unit 116, and outputs this recorded image data to the second color adjustment circuit 134. As a result, the recorded image is displayed on the second display device 224 via the second color adjustment circuit 134 and the second format converter 144. Subsequently, the processing proceeds to step S107.

When the second mode is determined as being selected in step S104, the processing proceeds to step S106. In step S106, the controller 160 instructs the selector interlock controller 154 to have the first selector 122 select the synthesized image between the observation image and the synthesized image as the first selected data. The first selector 122 acquires the image data of the synthesized image from the synthesizing circuit 118, and outputs this synthesized image data to the first color adjustment circuit 132 and the second selector 124. As a result, the synthesized image is displayed on the first display device 222 via the first color adjustment circuit 132 and the first format converter 142.

Furthermore, in step S106, the controller 160 instructs the selector interlock controller 154 to have the second selector 124 select the synthesized image between the synthesized image and the recorded image as the second selected data. The second selector 124 acquires the image data of the synthesized image from the first selector 122, and outputs this synthesized image data to the second color adjustment circuit 134. As a result, the synthesized image is displayed on the second display device 224 via the second color adjustment circuit 134 and the second format converter 144. Subsequently, the processing proceeds to step S107.

In step S107, the controller 160 has the first format converter 142 and the second format converter 144 convert the format of signals in compliance with the transmission standard to which the first display device 222 and the second display device 224 correspond. In other words, the controller 160 has the first format converter 142 perform output conforming to the transmission standard of the first display device 222, and has the second format converter 144 perform output conforming to the transmission standard of the second display device 224. The controller 160 has the first format converter 142 output the converted image data to the first display device 222. Furthermore, the controller 160 has the second format converter 144 output the converted image data to the second display device 224.

Generally, the shape of a terminal used to connect the first display device 222 and the second display device 224 with the display control device 100 differs depending on the transmission standard. Therefore, the first format converter 142 and the second format converter 144 perform format conversion by, for example, identifying the transmission standard corresponding to the terminal to which the display device is connected. Now, the present processing is ended.

According to the present embodiment, the display in the first mode and the display in the second mode may be appropriately selected. In the first mode, the observation image is displayed on the first display device 222 which is the main monitor, and the recorded image is displayed on the second display device 224 which is the sub-monitor. Since the observation image and the recorded image are displayed on different display devices, the observation image and the recorded image may each be displayed in a large size. Furthermore, by the monitor setting circuit 156 changing the setting of the first display device 222 and the second display device 224, in the case where the same image is displayed, the first display device 222 and the second display device 224 are adjusted to display a similar image. Alternatively, by the first color adjustment circuit 132 and the second color adjustment circuit 134 performing color adjustment of the observation image and the recorded image, in the case where the same image is displayed, the first display device 222 and the second display device 224 are adjusted to display a similar image. These adjustments include, for example, setting a color or contrast. As a result of these adjustments, even if different display devices are used for the first display device 222 and the second display device 224, the comparison between the observation image and the recorded image may be performed appropriately. For example, in the case of an observation image obtained by an endoscope, for example, since there is a difference in whether or not a blood vessel may be observed depending on whether these adjustments have or have not been performed, it is important that these adjustments are performed appropriately.

In the second mode, the recorded image recorded in the image recording unit 116 and the observation image are displayed side by side on the same first display device 222 and second display device 224, respectively. Since they are displayed on the same monitor, the observation image and the recorded image are displayed closely, allowing the comparison of these images to be easily performed. Since they are displayed on the same monitor, the observation image and the recorded image may be displayed under the same condition. Furthermore, adjustment is performed by the monitor setting circuit 156, or the first color adjustment circuit 132 and the second color adjustment circuit 134 so that a similar image may be displayed on the first display device 222 and the second display device 224. Therefore, information may be shared correctly between a person observing the first display device 222 and a person observing the second display device 224.

The transmission standard for the image data is converted by the first format converter 142 and the second format converter 144. Therefore, display devices with various types of transmission standards may be used for the first display device 222 and the second display device 224.

Second Embodiment

A second embodiment of the present invention will be explained. Here, the differences from the first embodiment will be explained. For identical portions, identical symbols will be applied, and the explanations thereof will be omitted. A schematic exemplary configuration of an endoscope system 1 according to the present embodiment is shown in FIG. 3. The configuration of the endoscope system 1 according to the present embodiment is similar to the endoscope system 1 according to the first embodiment except for the following matters.

In the endoscope system 1 according to the present embodiment, a first resolution converter 138 is provided between a first color adjustment circuit 132 and a first format converter 142. The first resolution converter 138 acquires color adjusted image data from the first color adjustment circuit 132. The first resolution converter 138 converts the resolution of the acquired image data in accordance with a resolution of an image to be displayed on a first display device 222. The first resolution converter 138 outputs the resolution converted image data to the first format converter 142. The first resolution converter 138 is connected to, for example, an input unit 152 and selects the resolution in accordance with an input to the input unit 152. The resolution of the image to be displayed on the first display device 222 is also limited by the transmission standard of the first display device 222. The first resolution converter 138 may also perform conversion by utilizing information related to the transmission standard of the first display device 222.

In a similar manner, in the endoscope system 1 according to the present embodiment, a second resolution converter 139 is provided between a second color adjustment circuit 134 and a second format converter 144. The second resolution converter 139 acquires color adjusted image data from the second color adjustment circuit 134. The second resolution converter 139 converts the resolution of the acquired image data in accordance with a resolution of an image to be displayed on a second display device 224. The second resolution converter 139 outputs the resolution converted image data to the second format converter 144. The second resolution converter 139 is connected to, for example, the input unit 152 and selects the resolution in accordance with an input to the input unit 152. The resolution of the image to be displayed on the second display device 224 is also limited by the transmission standard of the second display device 224. The second resolution converter 139 may also perform conversion by utilizing information related to the transmission standard of the second display device 224.

Figure 4A:
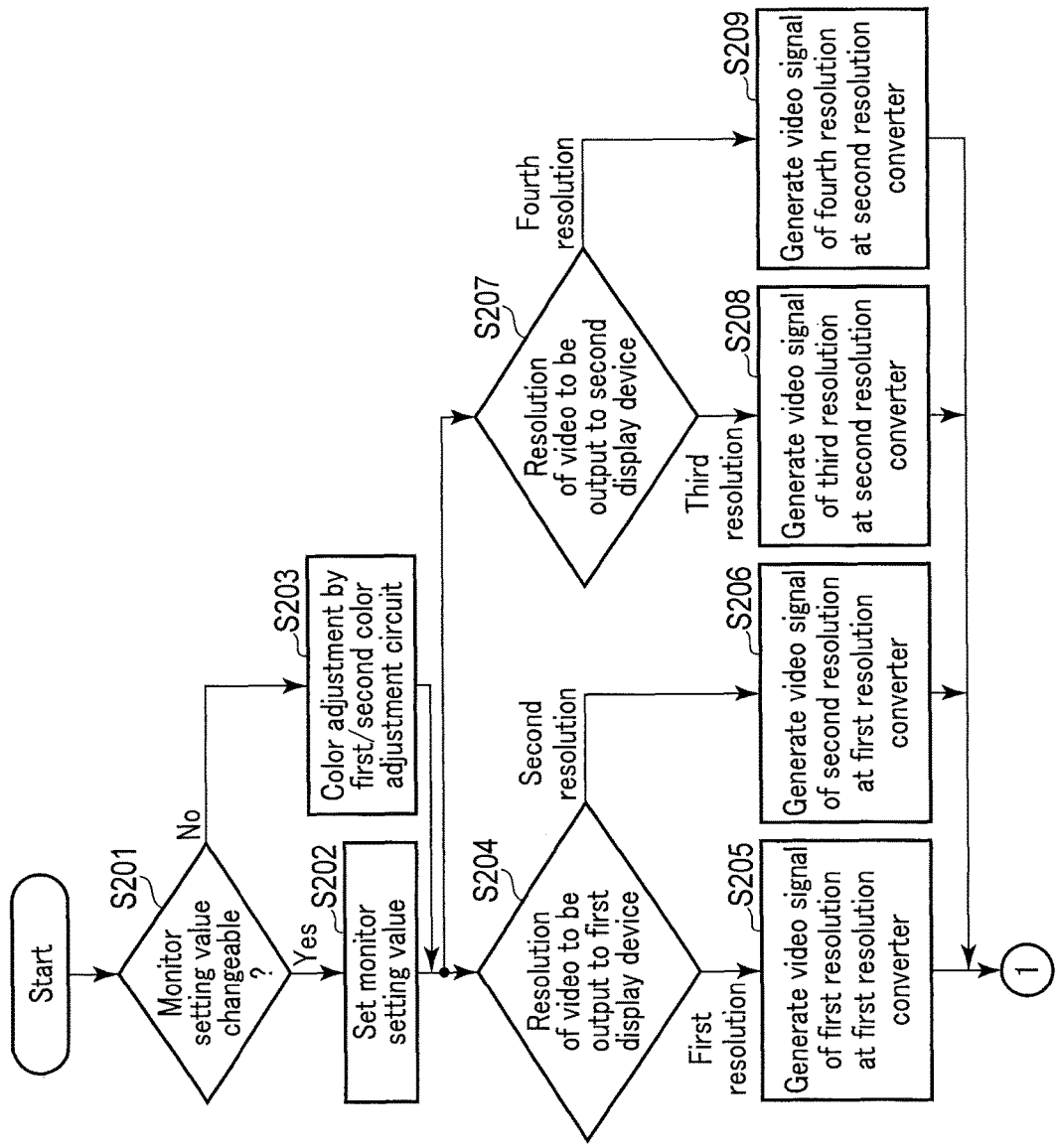
FIG. 4A is a flowchart showing an example of a display control by a display control device according to the second embodiment.
Figure 4B:
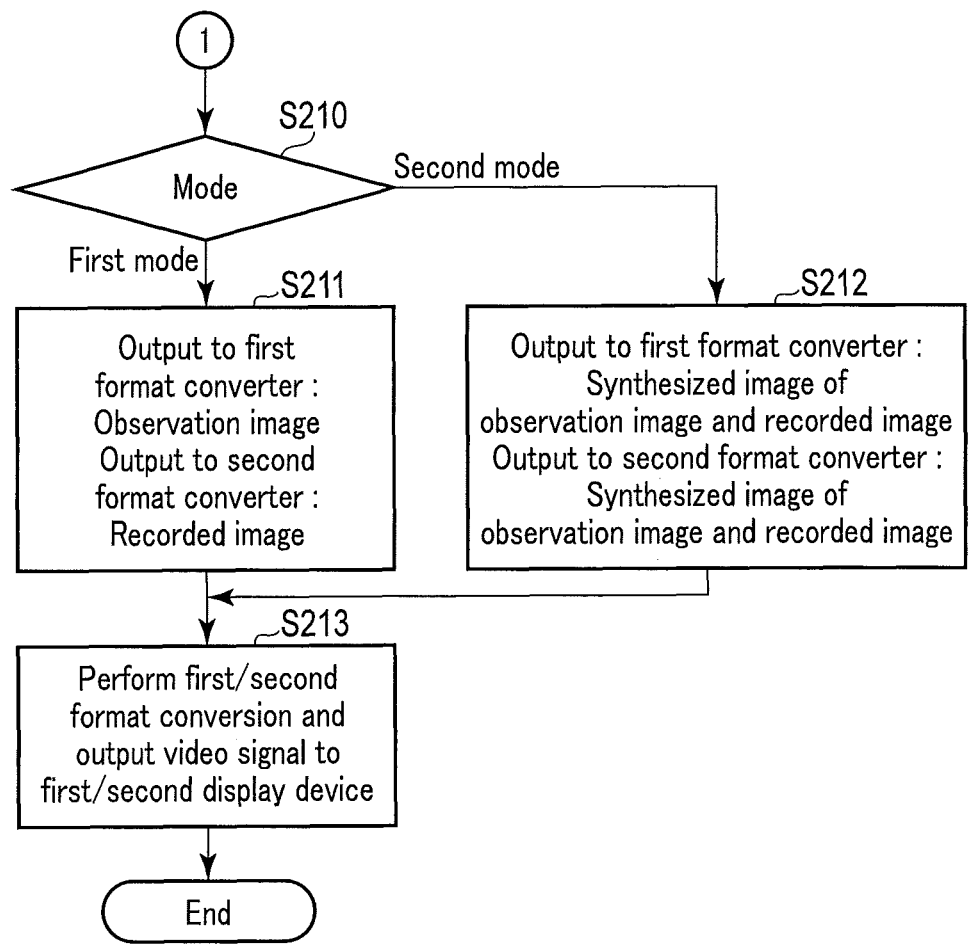
FIG. 4B is a flowchart showing an example of a display control by a display control device according to the second embodiment.

The operation related to the setting of the image display of the endoscope system 1 according to the present embodiment will be explained with reference to the flowchart shown in FIG. 4A and FIG. 4B. In the present operation, the processes in step S201 to step S203 are respectively the same as the processes in step S101 to step S103 of the first embodiment. Also, in the present operation, the processes in step S210 to step S213 are respectively the same as the processes in step S104 to step S107 of the first embodiment.

In step S201, the controller 160 determines whether or not the monitor setting value of the first display device 222 or the second display device 224 can be changed by the monitor setting circuit 156. If the monitor setting value is determined as being changeable, the processing proceeds to step S202. In step S202, the controller 160 has the monitor setting circuit 156 set the monitor setting values of the first display device 222 and/or the second display device 224. Subsequently, the processing proceeds to step S204 and S207. If the monitor setting value is determined as being unchangeable in step S201, the processing proceeds to step S203. In step S203, the controller 160 sets the first color adjustment circuit 132 and/or the second color adjustment circuit 134 so as to perform color adjustment. Subsequently, the processing proceeds to step S204 and step S207.

In step S204, the controller 160 determines the resolution of a video to output to the first display device 222. If the resolution of the video to be output to the first display device 222 is a first resolution, the processing proceeds to step S205. In step S205, the controller 160 has the first resolution converter 138 convert the resolution of the image data acquired from the first color adjustment circuit 132 into image data of the first resolution. Subsequently, the processing proceeds to S210.

In step S204, if the resolution of the video to be output to the first display device 222 is determined as being a second resolution, the processing proceeds to step S206. In step S206, the controller 160 has the second resolution converter 139 convert the resolution of the image data acquired from the second color adjustment circuit 134 into image data of the second resolution. Subsequently, the processing proceeds to S210.

In step S207, the controller 160 determines the resolution of a video to be output to the second display device 224. If the resolution of the video to be output to the second display device 224 is a third resolution, the processing proceeds to step S208. In step S208, the controller 160 has the second resolution converter 139 convert the resolution of the image data acquired from the second color adjustment circuit 134 into image data of the third resolution. Subsequently, the processing proceeds to S210.

If the resolution of a video to be output to the second display device 224 is determined as being a fourth resolution in step S207, the processing proceeds to step S209. In step S209, the controller 160 has the second resolution converter 139 convert the resolution of the image data acquired from the second color adjustment circuit 134 into image data of the fourth resolution. Subsequently, the processing proceeds to S210.

Here, a case in which the transmission standard of the first display device 222 is SDI, and the transmission standard of the second display device 224 is DVI is considered. At this time, for example, the following matters may be considered as the first resolution to the fourth resolution. In other words, for example, the first resolution may be HDTV (1920× 1080). Furthermore, for example, the second resolution may be SDTV (720×480). Furthermore, the third resolution may be 1920×1200. Furthermore, the fourth resolution may be 1280×1080. However, the first resolution to the fourth resolution may take any value as long as they satisfy the standards of the output to the display device. Accordingly, for example, the first resolution and the third resolution may be equal, and the second resolution and the fourth resolution may be equal.

In step S210, the controller 160 determines the selected display mode. If the first mode is determined as being selected, the processing proceeds to step S211.

In step S211, the controller 160 instructs a selector interlock controller 154 to have a first selector 122 select an observation image as first selected data. The controller 160 instructs the selector interlock controller 154 to have a second selector 124 select a recorded image as second selected data. Subsequently, the processing proceeds to step S213.

If the second mode is determined as being selected in step S210, the processing proceeds to step S212. In step S212, the controller 160 instructs the selector interlock controller 154 to have the first selector 122 select a synthesized image of the observation image and the recorded image as the first selected data. The controller 160 instructs the selector interlock controller 154 to have the second selector 124 select image data of the synthesized image as the second selected data. Subsequently, the processing proceeds to step S213.

In step S213, the controller 160 has the first format converter 142 and the second format converter 144 perform conversion of a signal format in compliance with the transmission standard corresponding to the first display device 222 and the second display device 224. This ends the present processing.

According to the present embodiment, the resolutions of the images to be displayed on the first display device 222 and the second display device 224 are selected appropriately in accordance with the transmission standards of the display device and the video signal, and applied resolution conversion. According to the present embodiment, images having the resolutions desired by a user may be displayed on the first display device 222 and the second display device 224.

Third Embodiment

The third embodiment of the present invention will be explained. Here, the differences from the first embodiment will be explained. For identical portions, identical symbols will be applied, and the explanations thereof will be omitted. A schematic exemplary configuration of an endoscope system 1 according to the present embodiment is shown in FIG. 5. The configuration of the endoscope system 1 according to the present embodiment is similar to the endoscope system 1 according to the first embodiment except for the following matters.

The display control device 100 of the endoscope system 1 according to the present embodiment is configured to be able to cope with a case in which display devices having a common output terminal but different transmission standards are connected. Therefore, the display control device 100 according to the present embodiment further comprises, in addition to the constituent elements of the display control device 100 according to the first embodiment, a third color adjustment circuit 136, a third format converter 146, and a third selector 126 downstream of the first selector 122.

The first selector 122 outputs the selected image data to the first color adjustment circuit 132, the third color adjustment circuit 136, and the second selector 124. The third color adjustment circuit 136 performs color adjustment processing on the image data to adjust the color of the image represented by the input image data. This color adjustment processing is a color adjustment performed in accordance with the characteristics of the first display device 222. The third color adjustment circuit 136 outputs the color adjusted image data to the third format converter 146.

The third format converter 146 performs processing for converting the transmission standard of the video signal. In other words, in compliance with the transmission standard to which the first display device 222 corresponds, the third format converter 146 performs processing for the image data input from the third color adjustment circuit 136 to comply with the transmission standard of the first display device 222. The third format converter 146 outputs the converted image data to the third selector 126.

The first format converter 142 performs processing for converting the transmission standard with respect to the image data input from the first color adjustment circuit 132, and outputs the processed image data to the third selector 126. Here, the transmission standard converted by the first format converter 142 and the transmission standard converted by the third format converter 146 are different standards.

The third selector 126 selects one of the image data acquired from the first format converter 142 and the image data acquired from the third format converter 146 in accordance with the input from the input unit 152. The third selector 126 outputs the selected data to the first display device 222 and has the image represented by the image data displayed on the first display device 222.

For example, a case is considered in which a coaxial cable is connected to the third selector using a BNC connector, and a DVI terminal is connected to the second format converter 144. A coaxial cable using a BNC connector is capable of transmitting signals based on both standards of, for example, an SDI signal and an analog composite signal. In this manner, a case may be assumed in which, for example, the transmission standard converted by the first format converter 142 is SDI, and the transmission standard converted by the third format converter 146 is an analog composite.

Figure 6:
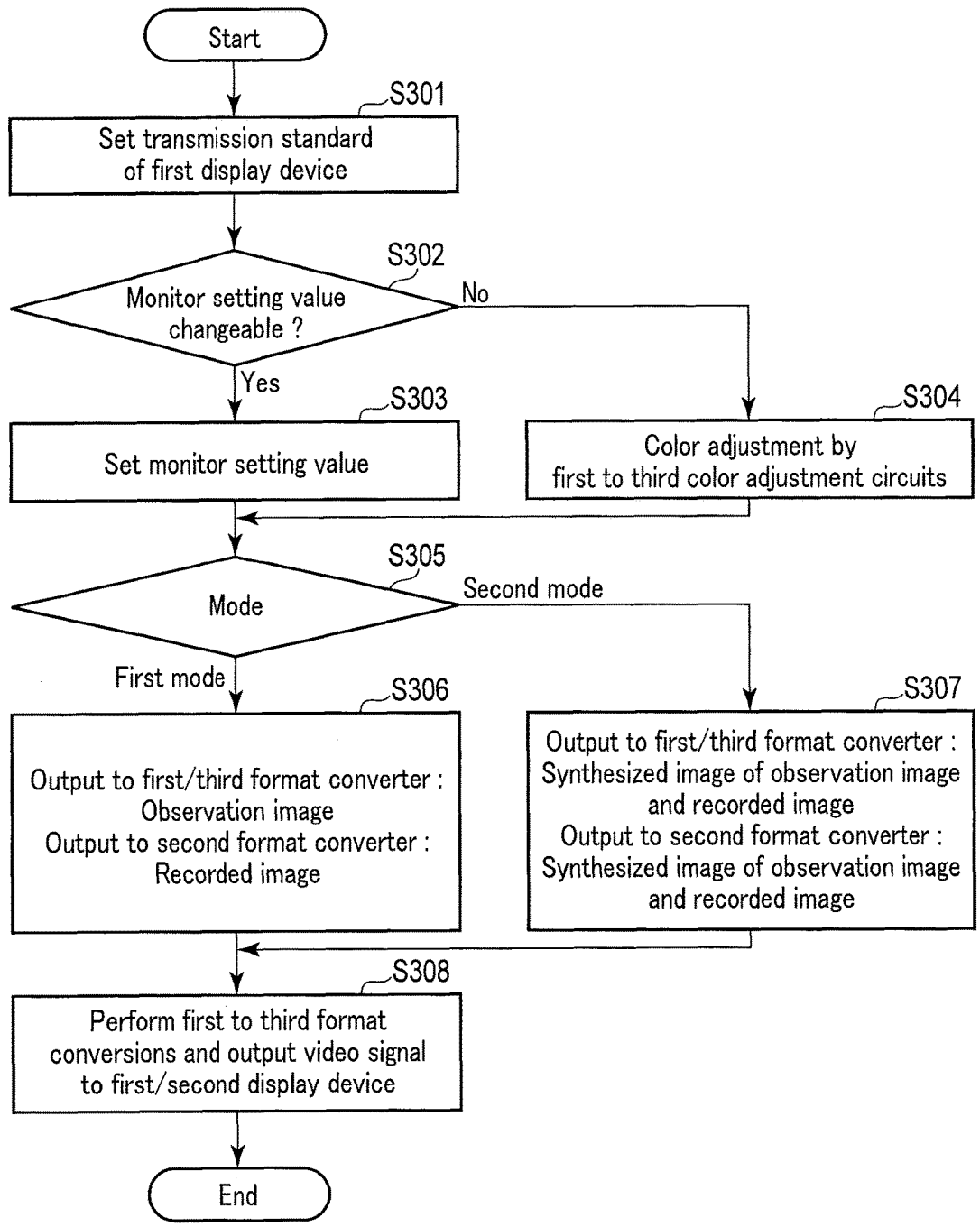
FIG. 6 is a flowchart showing an example of a display control by a display control device according to the third, embodiment.

The operation according to the setting of the image display of the endoscope system 1 according to the present embodiment will be explained with reference to the flowchart shown in FIG. 6. In the present operation, the processes in step S302 to step S305 are respectively the same as the processes in step S101 to step S104 according to the first embodiment. Furthermore, in the present operation, although the processes in step S306 to step S308 are respectively similar to the processes in step S105 to step S107 according to the first embodiment, they are different in that the image data input to the first display device 222 is processed by the first color adjustment circuit 132 and the first format converter 142, or is processed by the third color adjustment circuit 136 and the third format converter 146.

In step S301, the controller 160 acquires information related to the transmission standard of the first display device 222 and sets the transmission standard as a setting value. For example, when the cable connected to the first display device 222 is a coaxial cable, the output to this cable is decided whether to be the SDI signal or the analog composite signal.

In step S302, the controller 160 determines whether or not it is possible to change the monitor setting value of the first display device 222 or the second display device 224 by the monitor setting circuit 156. If the monitor setting value is determined as being changeable, the processing proceeds to step S303. In step S303, the controller 160 has the monitor setting circuit 156 set the monitor setting value of the first display device 222 and/or the second display device 224. Subsequently, the processing proceeds to step S305.

If the monitor setting value is determined as being unchangeable at the determination in step S302, the processing proceeds to steps S304. In step S304, the controller 160 sets the first color adjustment circuit 132, the third color adjustment circuit, and the second color adjustment circuit 134 so as to perform color adjustment. Here, whether the image data processed by the first color adjustment circuit 132 will be used or the image data processed by the third color adjustment circuit will be used depends on the transmission standard set in step S301. Subsequently, the processing proceeds to step S305.

In step S305, the controller 160 determines the selected display mode. If the first mode is determined as being selected, the processing proceeds to step S306.

In step S306, the controller 160 instructs the selector interlock controller 154 to have the first selector 122 select an observation image between the observation image and the synthesized image as the first selected data. The first selector 122 acquires the image data of the observation image from the image processing circuit 114 and outputs this observation image data to the first color adjustment circuit 132, the third color adjustment circuit, and the second selector 124.

The observation image data input to the first color adjustment circuit 132 is transmitted to the third selector 126 via the first format converter 142. In a similar manner, the observation image data input to the third color adjustment circuit 136 is transmitted to the third selector 126 via the third format converter 146.

In step S306, the controller 160 instructs the selector interlock controller 154 to have the second selector 124 select a recorded image between the observation image and the recorded image as the second selected data. The second selector 124 acquires the image data of the recorded image from the image recording unit 116, and outputs this recording image data to the second color adjustment circuit 134. As a result, the recorded image is displayed on the second display device 224 via the second color adjustment circuit 134 and the second format converter 144. Subsequently, the process proceeds to step S308.

If the second mode is determined as being selected in step S305, the processing proceeds to step S307. In step S307, the controller 160 instructs the selector interlock controller 154 to have the first selector 122 select a synthesized image between an observation image and the synthesized image as the first selected data. The first selector 122 acquires the image data of the synthesized image from the synthesizing circuit 118 and outputs this synthesized image data to the first color adjustment circuit 132, the third color adjustment circuit 136, and the second selector 124.

The synthesized image data input to the first color adjustment circuit 132 is input to the third selector 126 via the first format converter 142. In a similar manner, the synthesized image data input to the third color adjustment circuit 136 is input to the third selector 126 via the third format converter 146.

Furthermore, in step S307, the controller 160 instructs the selector interlock controller 154 to have the second selector 124 select a synthesized image between the synthesized image and a recorded image as the second selected data. The second selector 124 acquires the image data of the synthesized image from the first selector 122, and outputs this synthesized image data to the second color adjustment circuit 134. As a result, the synthesized image is displayed on the second display device 224 via the second color adjustment circuit 134 and the second format converter 144. Subsequently, the process proceeds to step S308.

In step S308, the controller 160 has the first format converter 142, the second format converter 144, and the third format converter 146 convert the formats of signals in compliance with the transmission standards to which the first display device 222 and the second display device 224 correspond. The image data whose transmission standard was converted at the first format converter 142, and the image data whose the transmission standard was converted at the third format converter 146 are transmitted to the third selector 126. Based on the transmission standard set in step S301, the third selector 126 outputs one of the image data acquired from the first format converter 142 and the image data acquired from the third format converter 146 to the first display device 222. For example, if the first display device 222 is a display device compatible with an SDI signal, the image data converted at the first format converter 142 is output to the first display device 222. On the other hand, if, for example, the first display device 222 is a display device compatible with an analog composite signal, the image data converted at the third format converter 146 is output to the first display device 222.

The controller 160 has the second format converter 144 output data that complies with the transmission standard of the second display device 224. The controller 160 has the second format converter 144 output the converted image data to the second display device 224. This ends the present processing.

According to the present embodiment, in the case where display devices having a common terminal shape but different transmission standards are connected to the display control device 100, image data may be converted into a transmission standard in compliance with the display device. In other words, even in the case where display devices having a common terminal shape but different transmission standards are connected, the display control device 100 of the present embodiment is capable of outputting the image data appropriately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A display control device for an endoscope comprising:
   an image acquiring unit which acquires observation image data from an imaging unit provided on the endoscope;
   an image recording unit which records recorded image data;
   an image synthesizing unit which generates synthesized image data representing a synthesized image obtained by synthesizing an image based on the observation image data and an image based on the recorded image data, based on the observation image data and the recorded image data;
   a first selector which selects one of the observation image data and the synthesized image data as first selected data, and outputs the first selected data to be displayed on a first display device;
   a second selector which selects one of the first selected data and the recorded image data recorded in the image recording unit as second selected data, and outputs the second selected data to be displayed on a second display device; and
   a selector interlock controller which interlocks and controls the first selector and the second selector.

2. The display control device according to claim 1, wherein, in a case where the selector interlock controller has the first selector select the observation image data as the first selected data, the selector interlock controller has the second selector select the recorded image data recorded in the image recording unit as the second selected data.

3. The display control device according to claim 1, wherein, in a case where the selector interlock controller has the first selector select the synthesized image data as the first selected data, the selector interlock controller has the second selector select the synthesized image data output from the first selector as the second selected data.

4. The display control device according to claim 1, wherein,
   in a case where the selector interlock controller has the first selector select the observation image data as the first selected data, the selector interlock controller has the second selector select the recorded image data recorded in the image recording unit as the second selected data; and
   in a case where the selector interlock controller has the first selector select the synthesized image data as the first selected data, the selector interlock controller has the second selector select the synthesized image data output from the first selector as the second selected data.

5. The display control device according to claim 1, further comprising a monitor setting circuit which adjusts a display setting of the first display device and a display setting of the second display device in a manner that a same image is displayed on the first display unit and the second display unit if the same image data is input to the first display device and the second display device.

6. The display control device according to claim 1, further comprising
   a first color adjustment circuit which performs color adjustment processing on the first selected data, and
   a second color adjustment circuit which performs color adjustment processing on the second selected data,
   wherein the color adjustment processing is a processing which has a same image displayed on the first display device and the second display device if the same image data is input to the first display device and the second display device.

7. The display control device according to claim 1, further comprising:
   a first format converter which converts a transmission standard of the first selected data so as to comply with a transmission standard used by the first display device; and
   a second format converter which converts a transmission standard of the second selected data so as to comply with a transmission standard used by the second display device.

8. The display control device according to claim 1 further comprising a plurality of format converters which have a transmission standard of the first selected data comply with each of plurality of transmission standards in a case where the plurality of transmission standards are used for a terminal of the same shape regarding the transmission standard used for the first display device.

9. The display control device according to claim 1, further comprising:
   a first resolution converter which adjusts resolution of an image displayed on the first display device; and
   a second resolution converter which adjusts resolution of an image displayed on the second display device.

10. The display control device according to claim 1, wherein the image recording unit records image data representing a still image based on the observation image data as the recorded image data.

11. An endoscope system comprising:
    a display control device according to claim 1;
    the endoscope;
    the first display device; and
    the second display device.

* * * * *